US00PP20533P3

(12) United States Plant Patent
Klemm

(10) Patent No.: US PP20,533 P3
(45) Date of Patent: Dec. 8, 2009

(54) ***BIDENS* PLANT NAMED 'KLEBF07003'**

(50) Latin Name: *Bidens ferulifolia*
Varietal Denomination: KLEBF07003

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/080,847

(22) Filed: Apr. 7, 2008

(65) Prior Publication Data

US 2009/0255021 P1 Oct. 8, 2009

(51) Int. Cl.
*A01H 5/00* (2006.01)

(52) U.S. Cl. ..... Plt./410

(58) Field of Classification Search ..... Plt./263, Plt./410

See application file for complete search history.

*Primary Examiner*—Annette H. Para
*Assistant Examiner*—Susan B McCormick Ewoldt
(74) *Attorney, Agent, or Firm*—Jondle & Associates, P.C.

(57) ABSTRACT

A new cultivar of *Bidens* plant particularly characterized by having large, yellow inflorescences, good branching, dense foliage and a homogenous plant habit, is disclosed.

1 Drawing Sheet

Genus and species: *Bidens ferulifolia.*
Variety denomination: 'KLEBF07003'.

BACKGROUND OF THE NEW PLANT

The present invention comprises a new and distinct cultivar of *Bidens,* botanically known as *Bidens ferulifolia*, and hereinafter referred to by the cultivar name 'KLEBF07003'. 'KLEBF07003' was discovered as a seedling resulting from an open pollination conducted in May 2004 in Stuttgart, Germany between the proprietary female *Bidens* parent, 'X 012' (unpatented) and an unknown individual *Bidens* plant. A single plant selection was subsequently chosen for further evaluation and for asexual propagation.

The new cultivar was created in 2004 in Stuttgart, Germany and has been asexually reproduced repeatedly by vegetative cuttings in Stuttgart, Germany over a two and one-half-year period. 'KLEBF07003' has been found to retain its distinctive characteristics through successive asexual propagations.

Plant Breeder's Rights for this cultivar were applied for in Switzerland on Mar. 30, 2007. 'KLEBF07003' has not been made publicly available more than one year prior to filing of this application.

SUMMARY OF THE INVENTION

The following are the most outstanding and distinguishing characteristics of this new cultivar when grown under normal commercial practices in a greenhouse in Stuttgart, Germany.

1. Large, yellow inflorescences;
2. Good branching;
3. Dense foliage; and
4. A homogenous plant habit.

DESCRIPTION OF THE PHOTOGRAPH

This new *Bidens* plant is illustrated by the accompanying photograph which shows buds, inflorescences and foliage; the colors shown are as true as can be reasonably obtained by conventional photographic procedures. The photograph is of a plant about 10-weeks old and grown from rooted cuttings in an 10-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEBF07003'. The data which define these characteristics were collected from asexual reproductions carried out in Stuttgart, Germany taken in the spring. The plant history was taken on 10-week old plants in 10-cm pots that were pinched once at the end of February and grown in a greenhouse. The color readings were determined under natural light. Color references are to The R.H.S. Colour Chart of The Royal Horticultural Society of London (R.H.S.) (2001).

DESCRIPTION OF THE NEW PLANT

Classification:
- *Family.*—Asteraceae.
- *Genus and species.*—*Bidens ferulifolia.*
- *Common name.*—*Bidens,* Beggarticks, Bur-marigold, tickseed.

Parentage:
- *Female parent.*—The proprietary *Bidens* parent, 'X 012' (unpatented).
- *Male parent.*—Unknown individual *Bidens* plant.

Plant:
- *Habit.*—Medium vigorous, trailing.
- *Height* (*from top of soil*).—13.0 cm.
- *Diameter* (*plant spread*).—28.0 cm.
- *Propagation.*—Vegetative propagation by cuttings.
- *Time to initiate and develop roots.*—3 weeks.
- *Root description.*—Fine, white.
- *Rooting habit.*—Moderate branching.

Branches:
- *Lateral branches* (*quantity per plant*).—10.
- *Length.*—4.0 cm to 6.0 cm.

*Diameter.*—0.1 cm.
*Internode length.*—0.5 cm to 1.5 cm.
*Texture.*—Smooth.
*Color.*—RHS 144B (Yellow-green) towards the lower part of the branches and becoming brown-reddish.

Leaves:
*Arrangement.*—Composite (leaflets lanceolate).
*Size.*—Length: 2.0 cm to 4.0 cm Width: 1.5 cm to 2.0 cm.
*Shape.*—Elliptical.
*Margin.*—Composed.
*Apex.*—Obtuse.
*Base.*—Absent.
*Color* (*both immature and mature*).—Upper surface: RHS 143B (Green) Lower surface: RHS 139C (Green).
*Texture* (*both surfaces*).—Smooth.
*Venation.*—Pinnate.
*Venation color* (*both surfaces for both immature and mature leaves*).—RHS 142C (Green).
*Petioles.*—Length: 1.0 cm to 2.0 cm Diameter: 1.0 cm Color (both upper and lower parts): Light green Texture: Smooth.

Inflorescence:
*Appearance.*—Daisy-type.
*Size.*—Diameter: 4.0 cm Depth: 0.5 cm.
*Diameter of disc.*—0.5 cm.
*Number of inflorescences and buds per plant.*—15 to 25.
*Lastingness of individual blooms on the plant.*—7 days.
*Fragrance.*—Absent.

Bud:
*Length.*—0.8 cm.
*Diameter.*—0.5 cm.
*Shape.*—Ovate.
*Color.*—RHS 146C (Yellow-green).

Ray florets:
*Length.*—2.0 cm.
*Width.*—1.0 cm.
*Shape.*—Elliptical.
*Apex.*—Obtuse.
*Margin.*—Entire.
*Number of ray florets per inflorescence.*—5.
*Color* (*when opening*).—Upper surface: RHS 9A (yellow) Lower surface: RHS 9A (yellow).
*Color* (*when fully opened*).—Upper surface: RHS 9A (yellow) Lower surface: RHS 9A (yellow).

Disc florets:
*Number or quantity per flower.*—5.
*Length.*—2.5 cm.
*Width.*—1.3 cm.
*Shape.*—Elliptical.

Phyllaries:
*Quantity per flower.*—Arranged in two rows with 5 close to the florets and 8 below.
*Length.*—0.6 cm.
*Width.*—0.1 cm for the 5 phyllaries close to the florets and 0.15 cm for the 8 phyllaries that are below.
*Color.*—RHS 161A (Greyed-yellow) for the 5 phyllaries close to the florets and RHS 143A (Green) for the 8 phyllaries that are below.
*Shape.*—Narrow lanceolate for the 5 phyllaries close to the florets and lanceolate for the 8 phyllaries that are below.

Fruit and seed set: Plant develops achenes with 2 awns.
Disease and insect resistance: Not observed.

COMPARISON WITH PARENTAL AND COMMERCIAL CULTIVARS

'KLEBF07003' differs from the female parent, the proprietary *Bidens* plant 'X 012' (unpatented) in that 'KLEBF07003' has larger inflorescences and leaves compared to 'X 012'.

'KLEBF07003' differs from the commercial comparison variety 'Sumbid 03' (U.S. Plant Pat. No. 17,900) in that 'KLEBF07003' has a shorter plant height of 13 cm compared to 'Sumbid 03' which has a plant height of 25 cm. In addition, 'KLEBF07003' has 5 elliptical ray florets, while 'Sumbid 03' has about 7 to 8 ovate ray florets. Also, 'KLEBF07003' has an inflorescence disc diameter of 0.5 cm, while 'Sumbid 03' has a larger inflorescence disc diameter of 0.8 cm.

I claim:

1. A new and distinct cultivar of *Bidens* plant as shown and described herein.

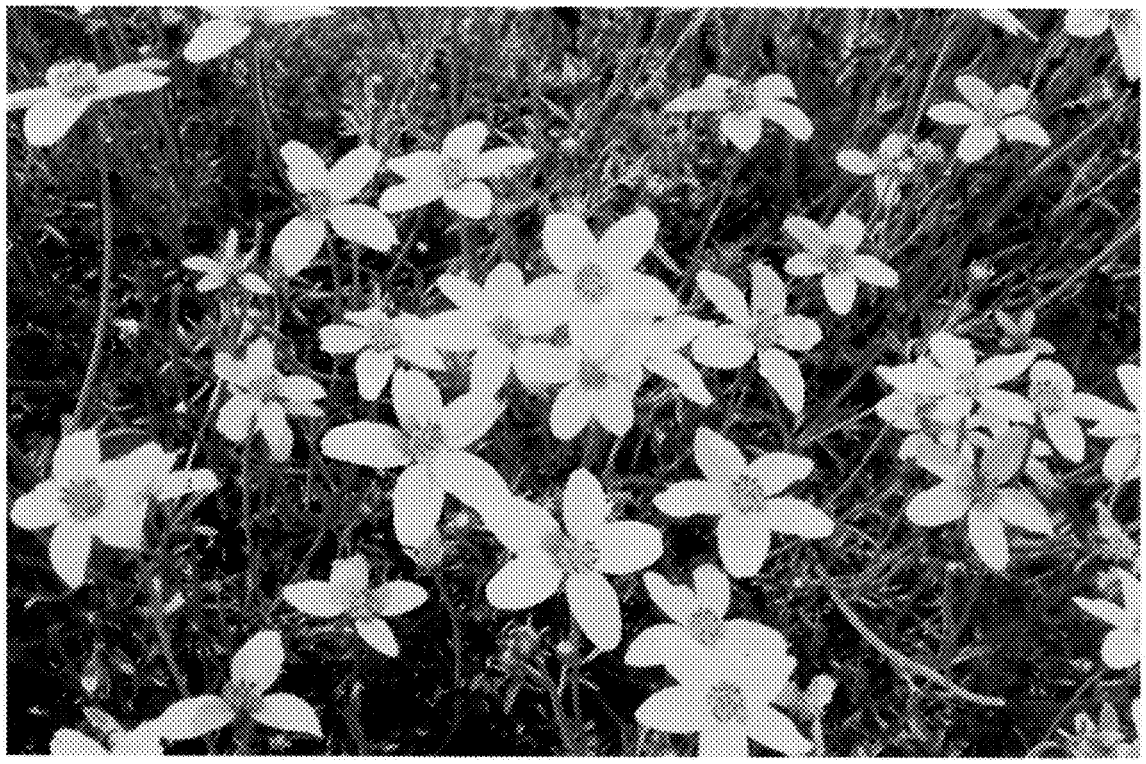

* * * * *